United States Patent
Papangelou et al.

(10) Patent No.: US 10,646,234 B2
(45) Date of Patent: May 12, 2020

(54) MENISCAL PROBE CUTTER

(71) Applicant: Arthrex, Inc., Naples, FL (US)

(72) Inventors: Christopher G. Papangelou, Bonita Springs, FL (US); Brandon L. Roller, Naples, FL (US); Sean Murphy, Boise, ID (US)

(73) Assignee: Arthrex, Inc., Naples, FL (US)

( * ) Notice: Subject to any disclaimer, the term of this patent is extended or adjusted under 35 U.S.C. 154(b) by 475 days.

(21) Appl. No.: 14/453,267

(22) Filed: Aug. 6, 2014

(65) Prior Publication Data

US 2015/0045797 A1    Feb. 12, 2015

Related U.S. Application Data

(60) Provisional application No. 61/863,338, filed on Aug. 7, 2013.

(51) Int. Cl.
*A61B 17/16*    (2006.01)
*A61B 17/3207*    (2006.01)
(Continued)

(52) U.S. Cl.
CPC .... *A61B 17/1611* (2013.01); *A61B 17/00234* (2013.01); *A61B 17/320016* (2013.01);
(Continued)

(58) Field of Classification Search
CPC ............ A61B 17/1633; A61B 17/1608; A61B 17/1606; A61B 17/1604; A61B 17/16; A61B 17/320016; A61B 17/32053; A61B 17/320783; A61B 17/320064; A61B 17/320036; A61B 17/3205
(Continued)

(56) References Cited

U.S. PATENT DOCUMENTS 539,309 A  *  5/1895  Seybold ................... A61D 1/06
                                                              606/137
3,844,272 A  *  10/1974  Banko ................ A61B 10/0266
                                                              600/566
(Continued)

FOREIGN PATENT DOCUMENTS

EP    1 110 520 A1    6/2001
WO   WO-2012/089767 A1    7/2012

OTHER PUBLICATIONS

Examination Report for European Patent Application No. 14752732.9 dated Feb. 20, 2020.

*Primary Examiner* — David W Bates
(74) *Attorney, Agent, or Firm* — Carlson, Gaskey & Olds, P.C.

(57) ABSTRACT

Instruments and methods that allow for a minimally invasive way to probe, locate, and cut a meniscus during a meniscectomy procedure. The instrument is a single hybrid probe/cutter instrument provided with both probing and cutting means that allow probing and cutting of the meniscus with the same hybrid instrument. A minimally invasive technique for probing and cutting (resecting) a torn area of a meniscus by employing the single, hybrid probing/cutting instrument is also provided. The technique provides a consistently good-quality meniscus with improved cosmetic results, and is simple and easily reproducible, strong, and time-saving for meniscal repairs.

24 Claims, 5 Drawing Sheets

(51) Int. Cl.
*A61B 17/32* (2006.01)
*A61B 17/3211* (2006.01)
*A61B 17/00* (2006.01)
(52) U.S. Cl.
CPC ........... *A61B 17/320783* (2013.01); *A61B 2017/00238* (2013.01); *A61B 2017/32113* (2013.01)
(58) Field of Classification Search
USPC .......................................................... 606/171
See application file for complete search history.

(56) References Cited

U.S. PATENT DOCUMENTS

| | | | | |
|---|---|---|---|---|
| 3,902,498 A | * | 9/1975 | Niederer | A61B 17/1611 606/170 |
| 3,995,619 A | * | 12/1976 | Glatzer | A61B 10/0275 600/550 |
| 4,006,746 A | * | 2/1977 | Edwards | A61B 17/322 606/167 |
| 4,473,076 A | * | 9/1984 | Williams | A61F 9/0133 30/320 |
| 4,497,320 A | * | 2/1985 | Nicholson | A61B 17/32 606/170 |
| 4,517,977 A | * | 5/1985 | Frost | A61B 17/32002 604/22 |
| 4,586,497 A | * | 5/1986 | Dapra | A61B 17/1671 606/180 |
| 4,678,459 A | * | 7/1987 | Onik | A61B 17/32002 604/22 |
| 4,733,662 A | * | 3/1988 | DeSatnick | A61B 17/320016 30/162 |
| 4,924,882 A | * | 5/1990 | Donovan | A61B 17/32 128/898 |
| 5,253,659 A | * | 10/1993 | McNamara | A61B 17/320016 128/898 |
| 5,292,330 A | * | 3/1994 | Shutt | A61B 17/320016 606/167 |
| 5,323,765 A | * | 6/1994 | Brown | A61B 17/320036 128/898 |
| 5,443,474 A | * | 8/1995 | Sfakianos | A61B 17/320016 30/294 |
| 5,451,227 A | * | 9/1995 | Michaelson | A61B 17/1611 606/170 |
| 5,549,623 A | * | 8/1996 | Sharpe | A61B 17/320016 600/564 |
| 5,569,283 A | * | 10/1996 | Green | A61B 17/320036 30/162 |
| 5,582,618 A | * | 12/1996 | Chin | A61B 17/1611 606/170 |
| 5,658,302 A | * | 8/1997 | Wicherski | A61B 17/32075 604/22 |
| 5,669,922 A | * | 9/1997 | Hood | A61B 17/320068 606/169 |
| 5,720,760 A | * | 2/1998 | Becker | A61B 17/32002 606/167 |
| 5,735,865 A | * | 4/1998 | Schaumann | A61B 1/317 600/101 |
| 5,755,718 A | * | 5/1998 | Sklar | A61B 17/1604 606/170 |
| 5,873,886 A | * | 2/1999 | Larsen | A61B 10/04 606/159 |
| 5,893,861 A | * | 4/1999 | Yumoto | A61B 17/320036 606/167 |
| 5,957,944 A | * | 9/1999 | Khuri | A61B 17/3211 128/898 |
| 5,968,061 A | * | 10/1999 | Mirza | A61B 17/320036 604/171 |
| 6,261,294 B1 | * | 7/2001 | Stihl | A61B 17/1608 606/170 |
| 6,280,447 B1 | * | 8/2001 | Marino | A61B 17/025 606/170 |
| 7,674,266 B2 | * | 3/2010 | Lieberman | A61B 17/1604 606/167 |
| 7,896,879 B2 | * | 3/2011 | Solsberg | A61B 17/0401 606/79 |
| 8,608,763 B1 | * | 12/2013 | Jurbala | A61B 17/320036 606/170 |
| 8,764,835 B2 | * | 7/2014 | Ferree | A61F 2/44 606/144 |
| D737,342 S | * | 8/2015 | Ng | D15/78 |
| D753,826 S | * | 4/2016 | Eggeling | D24/147 |
| 10,154,852 B2 | * | 12/2018 | Conlon | A61B 17/320068 |
| 2004/0054378 A1 | * | 3/2004 | Yang | A61B 17/320036 606/191 |
| 2004/0215201 A1 | * | 10/2004 | Lieberman | A61B 17/00234 606/93 |
| 2006/0004369 A1 | * | 1/2006 | Patel | A61B 17/1633 606/79 |
| 2006/0030785 A1 | * | 2/2006 | Field | A61B 10/02 600/567 |
| 2007/0255298 A1 | | 11/2007 | Djordjevic et al. | |
| 2007/0288043 A1 | | 12/2007 | Rehnke | |
| 2008/0114364 A1 | * | 5/2008 | Goldin | A61B 17/1617 606/79 |
| 2008/0161809 A1 | * | 7/2008 | Schmitz | A61B 17/1604 606/79 |
| 2009/0234452 A1 | * | 9/2009 | Steiner | A61B 17/1764 623/14.12 |
| 2010/0100046 A1 | * | 4/2010 | Berger | A61B 17/320036 604/164.12 |
| 2013/0079804 A1 | | 3/2013 | Milton et al. | |
| 2013/0144292 A1 | * | 6/2013 | To | A61B 17/3205 606/79 |
| 2013/0211201 A1 | * | 8/2013 | Wongsiri | A61B 17/02 600/202 |
| 2014/0171790 A1 | * | 6/2014 | Guo | A61B 17/320036 600/424 |
| 2017/0172604 A1 | * | 6/2017 | Denham | A61B 17/32053 |
| 2017/0238958 A1 | * | 8/2017 | Lown | A61B 17/320036 |

* cited by examiner

US 10,646,234 B2

MENISCAL PROBE CUTTER

CROSS-REFERENCE TO RELATED APPLICATIONS

This application claims the benefit of U.S. Provisional Application No. 61/863,338, filed Aug. 7, 2013, the disclosure of which is incorporated by reference in its entirety herein.

FIELD OF THE INVENTION

The present invention relates to the field of surgery and, more particularly, to instruments and methods of probing and cutting tissue such as meniscal tissue.

BACKGROUND OF THE INVENTION

A meniscectomy procedure is typically performed to remove torn segments of a meniscus or to release a meniscus. During the procedure, a miniature camera is inserted through a small incision to allow the orthopedic surgeon to insert surgical instruments such as probes and cutters through other small incisions to probe around the meniscal area, locate any tear, and trim or repair the tear.

There is a need for instruments and techniques for probing and locating a meniscus tear, and cutting a tear of the meniscus at the desired location, with minimal error and by simplified methods and instruments. An instrument designed to both probe and cut a meniscus is also needed. Also needed are minimally invasive techniques for probing/locating/cutting a meniscus that are safe, provide a consistently good-quality meniscal cut with high cosmetic results, and are simple and easily reproducible. Methods and instruments for delivering a "protected" cutting edge to a precise location (and then using a single device to probe a joint and deliver a precise cut without damaging/cutting the surrounding articular surfaces and structures) are also needed.

SUMMARY OF THE INVENTION

The present invention provides instruments and methods that allow for a minimally invasive way to probe, locate, and cut a meniscus during a meniscectomy procedure. The instrument of the present invention is a hybrid probe/cutter instrument provided with both probing and cutting means that allow probing and cutting of the meniscus with the same hybrid instrument.

The present invention also provides a minimally invasive technique for probing and cutting (resecting) a torn area of a meniscus by employing a single, hybrid probing/cutting instrument. The technique provides a consistently good-quality meniscus with improved cosmetic results, and is simple and easily reproducible, strong, and time-saving for meniscal repairs.

These and other features and advantages will become apparent from the following description that is provided in connection with the accompanying drawings and illustrated embodiments.

DETAILED DESCRIPTION OF THE PREFERRED EMBODIMENTS

The present invention provides surgical systems and methods for meniscal repairs. A hybrid combined probe/cutter instrument is provided with dual means for probing and cutting a torn meniscus. The instrument is a cannulated (fully or partially) meniscal probe or meniscal trimmer that has a cutting device/blade placed through the cannulation to cut tissue. The hybrid instrument allows a surgeon to probe tissue and insert the blade once the desired location has been determined, and then cut/trim the tissue without removing the probe.

The present invention also provides methods of meniscal repair by the steps of: (i) providing a hybrid (combined) probe/cutter instrument; and (ii) employing the hybrid (combined) probe/cutter instrument to both probe and cut/resect the meniscus.

The present invention also provides devices and methods that allow for delivering a "protected" cutting edge to a precise location. A single device can then be used to probe a joint and deliver a precise cut without damaging/cutting surrounding articulating surfaces and structures.

As detailed below, the invention provides a single device used to hook the meniscus and cut a tear or the meniscus at desired location. The device is in the form of a cannulated meniscal probe that can have a cutting device placed through the cannulation to cut tissue. The device allows a surgeon to probe tissue and insert blade once the surgeon has found the desired location and cut the tissue without removing the probe. In an exemplary embodiment, the device comprises a handle and an outer probe tip shaft. The handle and the shaft are preferably reusable. The inner blade is preferably "single use" and is configured to snap into the handle and slide along the track in the handle. The device tip may be an exemplary cannulated 2.5 mm probe tip with a blade that slides into a slot formed (machined) into the probe tip. The assembled device in its original configuration has the cutting blade not exposed.

Figure 1:
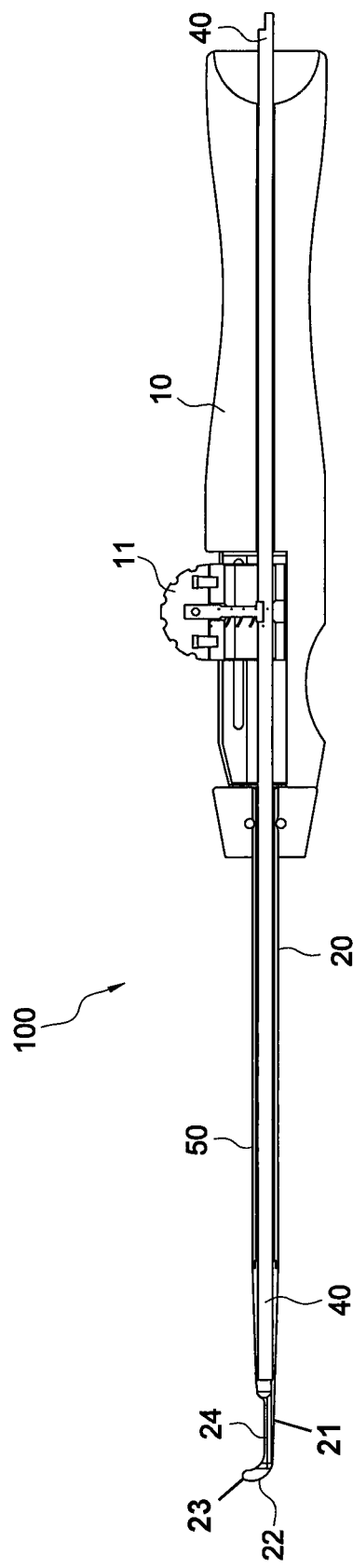
FIGS. 1-4 illustrate various schematic views of a hybrid meniscal probe cutter according to an exemplary embodiment of the present invention.

Referring now to the drawings, where like elements are designated by like reference numerals, FIGS. 1-4 illustrate an exemplary instrument 100 of the present invention. Instrument 100 is a hybrid probe/cutter provided with a probe 50 comprising a handle 10 (for example, a grip handle 10 with an actuating mechanism 11) that is fully or partially cannulated and an outer tube or shaft 20 connected to the handle. Outer tube or shaft 20 is also fully or partially cannulated and is provided with distal end 22 having probing means 22 (for example, probing tip 22) to allow probing and/or hooking of tissue to be examined and repaired. As shown in FIG. 1, the probing means 22 includes a longitudinal portion 21 and a curved portion 23 extending from the longitudinal portion 21, and the longitudinal portion 21 does not extend outside a diameter of the outer tube 20 relative to a longitudinal axis.

In an exemplary embodiment, the outer tube or shaft 20 of probe 50 houses an inner cutting instrument 40 which may be in the form of a cutting blade, for example, an inner cutting blade. As detailed below, the probing tip 22 of probe 50 probes and hooks the tissue so that, upon actuation and advancement, the inner cutting blade 40 then cuts/trims/scopes the tissue to remove any torn area of the tissue. Blade 40 may be a single-use, disposable blade for a single-use insertion and single-use with probe 50. The probe 50 (the handle and outer probe tip shaft) may be reusable.

Figure 2:
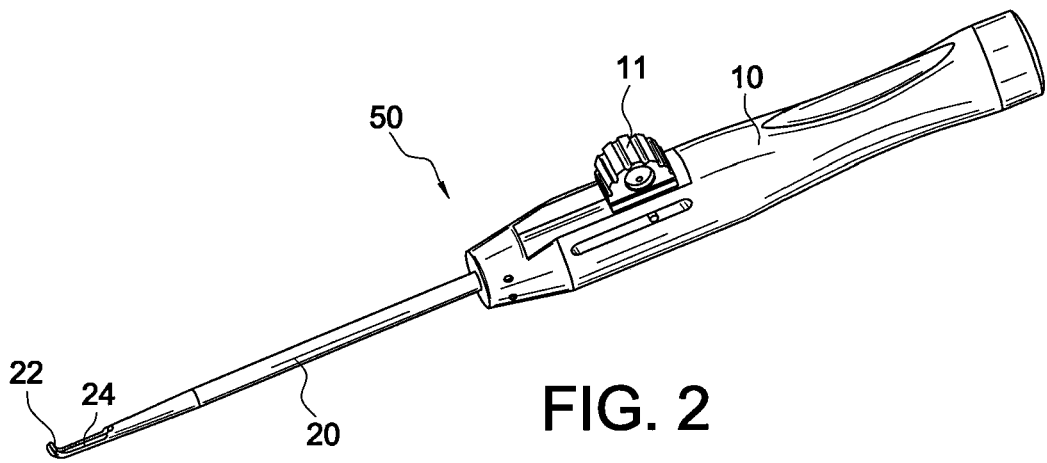
Figure 3:
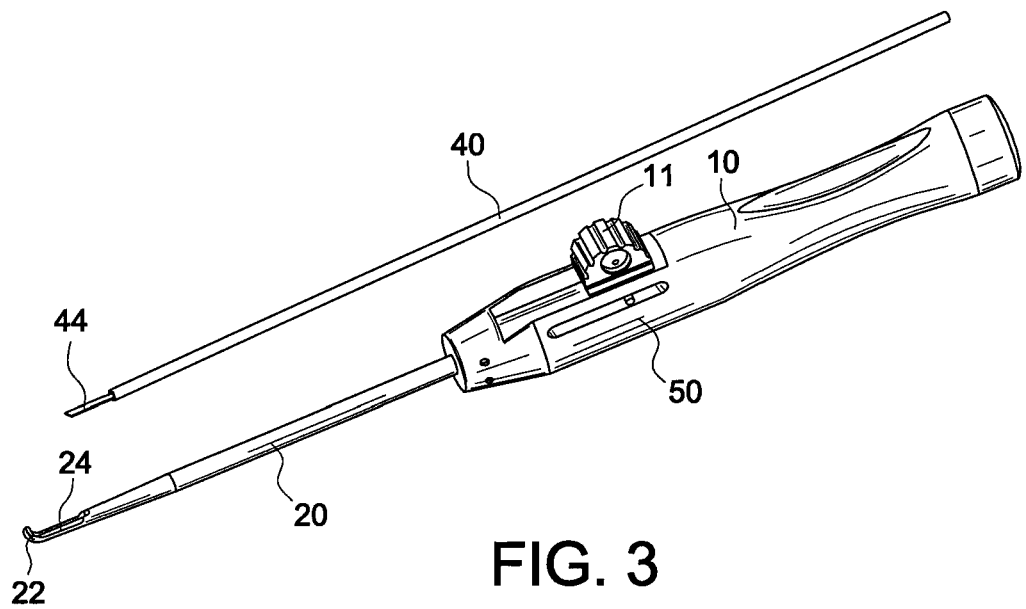
Figure 4:
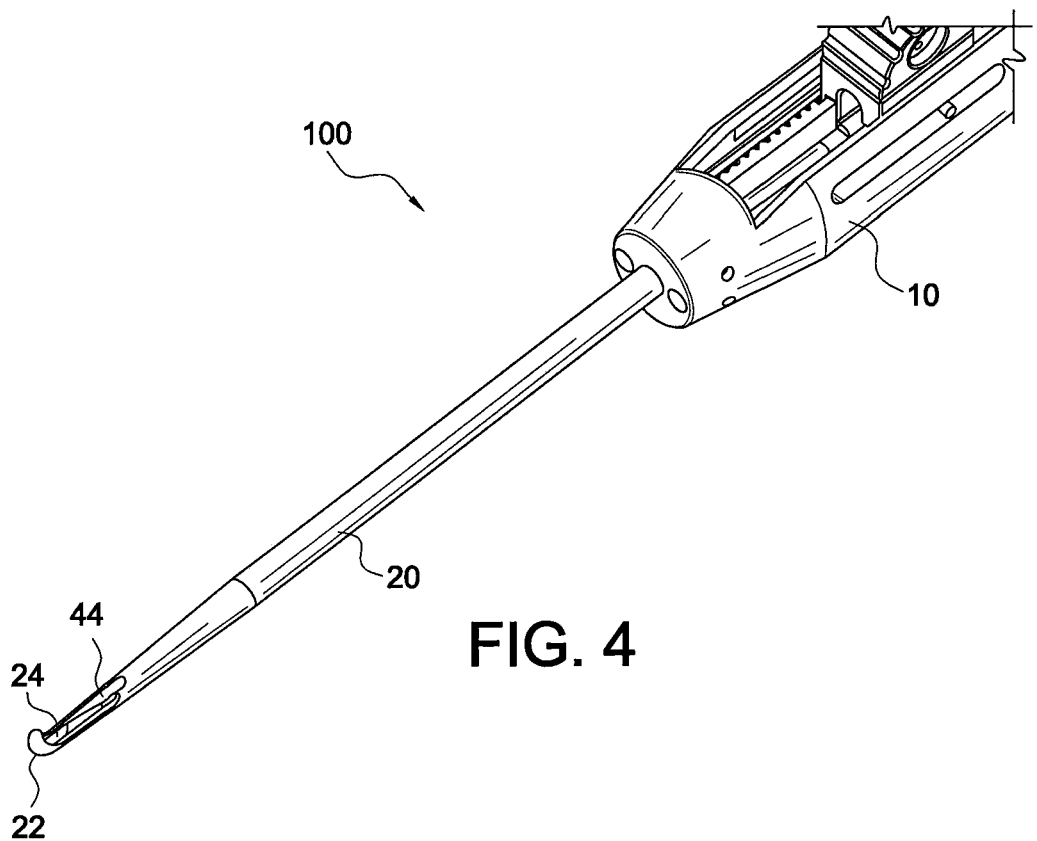

FIG. 1 illustrates instrument 100 with inner cutting blade 40 assembled with the probe 50, i.e., passing through cannulated outer tube 20 and handle 10 of probe 50. FIG. 2 shows only the probe 50 without the cutting blade 40. FIG. 3 depicts an exploded view of instrument 100 with the probe 50 and cutting blade 40 in the unassembled state. FIG. 4 shows an enlarged view of the distal end of the hybrid instrument 100, showing most distal end 44 of cutting instrument 40 extending through an elongated window 24 of probing means 22 of probe 50. Probing means 22 is an exemplary probe tip or probing tip 22 that is provided with an elongated slot 25 (shown more clearly in FIG. 6) formed within the probe tip 22 to allow cutting blade 40 to pass/slide therethrough. The curved portion 23 of the probing means 22 extends outside the diameter of the shaft 20 relative to the longitudinal axis.

Figure 5:
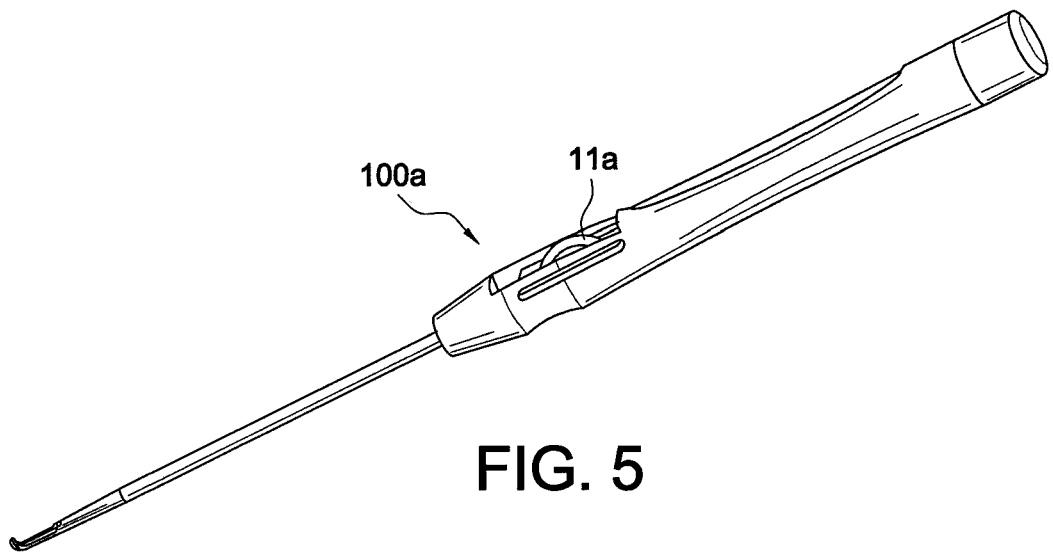
FIG. 5 illustrates a perspective view of a hybrid meniscal probe cutter according to another exemplary embodiment of the present invention.

FIG. 5 illustrates another embodiment of a hybrid (combined) probe/cutter instrument 100a of the present invention which is similar to instrument 100 of FIGS. 1-4 but differs in the configuration of actuating mechanism 11a to actuate the blade 40.

Cutting blade 40 may be assembled with (loaded or inserted into) the probe 50 by any known methods in the art. In an exemplary-only embodiment, the probe 50 is fully cannulated (i.e., both handle 10 and shaft 20 are fully cannulated) and the blade is inserted from a most proximal end of the handle all the way through the probing tip 22. Upon assembly, the blade 40 may be either in a retracted, non-cutting, non-exposed or first position (when probing of tissue is conducted with the probing tip 22) or in an actuating, cutting, exposed or second position (when cutting of the torn meniscus is conducted with the cutting blade). Manipulation of actuating mechanism 11 on handle 10 allows actuation of the blade 40 from the first position to the second position and vice-versa. Various sized blades can be attached to strip/cut different width and depth meniscal sizes and shape variations.

Figure 6:
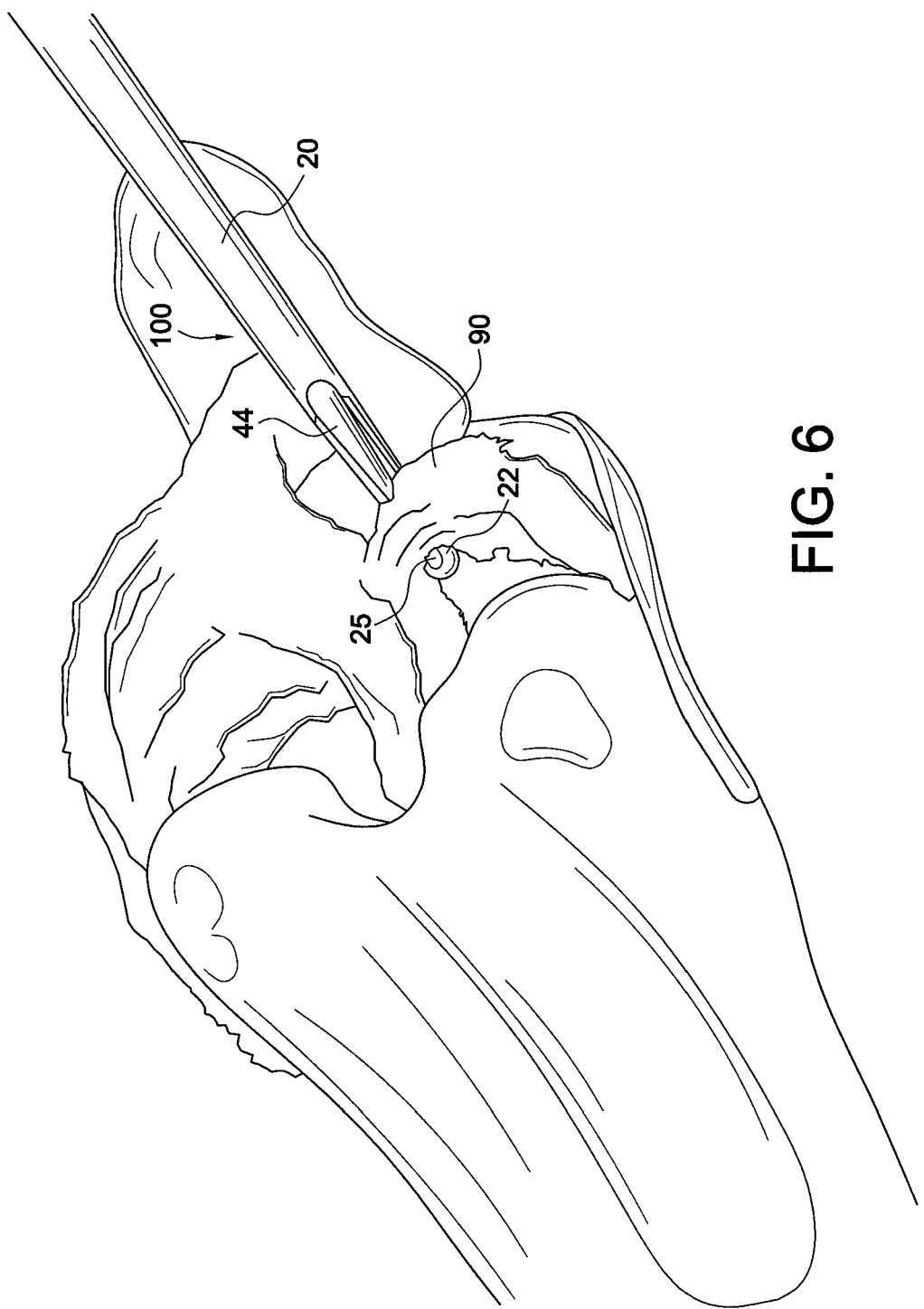
FIG. 6 illustrates the hybrid meniscal probe cutter of FIG. 1 used on a meniscal repair according to an exemplary embodiment of the present invention.

FIG. 6 illustrates an exemplary torn knee meniscus 90 that is repaired with exemplary hybrid (combined) probe/cutter instrument 100 of the present invention. Once inserted into the knee joint, the probe 50 probes around the meniscal area and locates the torn meniscus, also hooking onto the torn meniscal parts. Blade 40 is then actuated (from a retracted, non-cutting or first position to an actuating, cutting or second position) to allow cutting off (snipping) any of the torn meniscal part of meniscus 90. During the probing operation, the blade is kept recessed (retracted or non-exposed in the first position) and then advanced to the second position to cut tissue. In this manner, the single device/instrument of the present invention is used to probe and hook the meniscus and then cut the tear in the meniscus at the desired location.

The probe 50 and blade 40 may be interchangeable with each other, may be removable, may be sterilizable (autoclavable), and may be provided as single-use only devices (disposable) or as multiple-use devices. In particular applications, the blade 40 and probe 50 may be designed so that one may be snapped onto the other while the other may be snapped out of the other (or vice-versa). The blade 40 may be also designed so that it can be removed from the probe 50.

Figure 7:
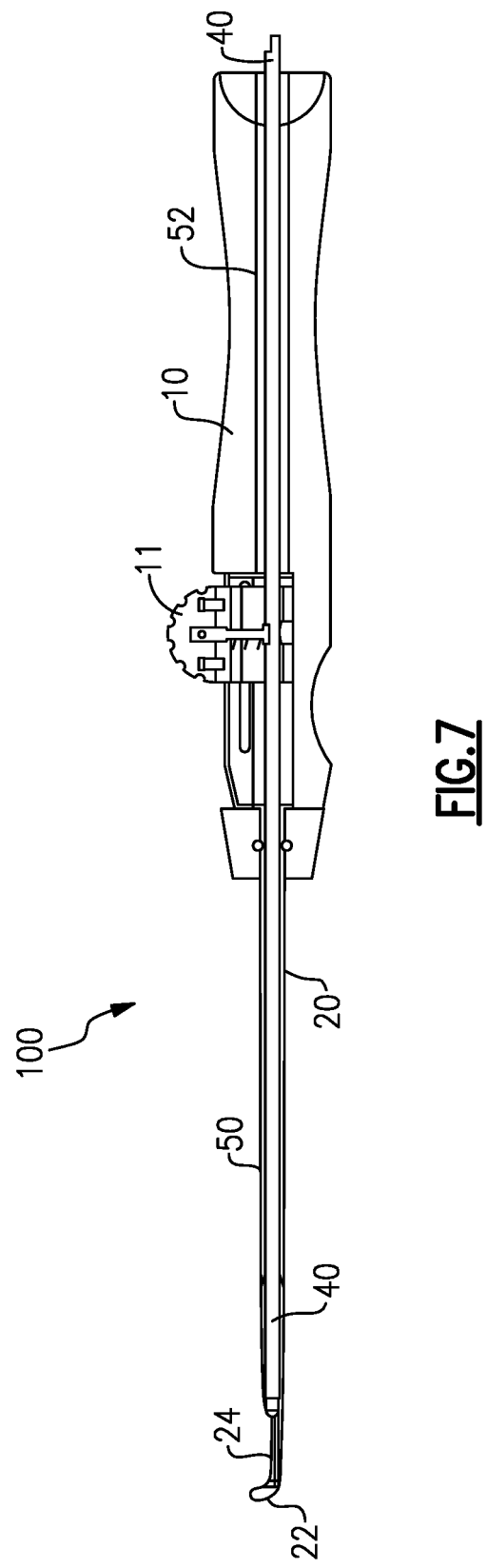
FIG. 7 illustrates the hybrid meniscal probe cutter of FIG. 1 including a track in which the cutting device can slide.

The handle and the shaft are preferably reusable. The inner blade is preferably "single use" and is configured to snap into the handle and slide along the track 52 in the handle. As shown in FIG. 7, device tip may be an exemplary cannulated 2.5 mm probe tip with a blade that slides into a slot formed (machined) into the probe tip. The assembled device in its original configuration has the cutting blade not exposed.

The present invention also provides a method of soft tissue repair with instrument 100, 100a of FIGS. 1-5. According to an exemplary only embodiment, a method of sizing and cutting a torn meniscus to desired dimensions (i.e., width and length) comprises the steps of: (i) providing a hybrid (combined) probe/cutter instrument 100, 100a; and (ii) employing the hybrid (combined) probe/cutter instrument 100, 100a to both probe and cut/resect a torn meniscus.

The present invention provides a minimally invasive techniques for probing and cutting (resecting) a meniscus by employing a single hybrid probe/cutter instrument 100, 100a. The techniques provide a consistently good-quality graft with improved cosmetic results, and are simple and easily reproducible while saving time for meniscal repairs. The techniques and instruments 100, 100a of the present invention allow for delivering a "protected" cutting edge to a precise location. In this manner, a single device can be used to probe a joint and deliver a precise cut without damaging/cutting surrounding articulating surfaces and structures.

The instrument 100, 100a may be employed for various tissue repairs, for example, in veterinary applications to cut and release the meniscus, and/or in hip applications in humans to hook any torn pieces of cartilage (labral or acetabular tear) around the acetabulum in the hip socket and then snip them off (cut around the margins) to address hip conditions that cause pain, stiffness, and other disabling symptoms of the hip joint. The instrument 100, 100a may be also employed in any other ligament/tendon/graft reconstructions known in the art, for example, ACL reconstructions among many others.

While the present embodiments are described herein with reference to illustrative figures for particular applications, it should be understood that the embodiments are not limited thereto. Those having ordinary skill in the art and access to the teachings provided herein, will recognize additional modifications, applications, embodiments and substitution of equivalents all falling within the scope of the presented embodiments.

What is claimed is:

1. A hybrid probe/cutter instrument for meniscal probing and cutting, comprising:
   a handle;
   an outer tube attached to the handle and stationary relative to the handle, the outer tube having a proximal end, a distal end, a diameter, and a longitudinal axis;
   a probe tip comprising a hook at a most distal end of the outer tube and configured to hook tissue, wherein a most distal surface of the hook of the outer tube is curved, the hook comprises a longitudinal portion having an elongated slot and a curved portion extending from the longitudinal portion having another slot to receive a cutting device, and the longitudinal portion does not extend outside the diameter of the outer tube relative to the longitudinal axis;
   the cutting device extending through the outer tube and housed within the outer tube, the cutting device configured to move within the elongated slot of the longitudinal portion from a first position proximal to the probe tip in which the cutting device is housed inside the outer tube to a second position in which the cutting device is received within the elongated slot formed in the probe tip, is nested within the another slot, and is exposed for cutting the tissue; and an actuator mechanism for actuating the cutting device from the first position to the second position.

2. The hybrid probe/cutter instrument of claim 1, wherein the actuator mechanism is on or within the handle.

3. The hybrid probe/cutter instrument of claim 1, wherein the cutting device includes a cutting blade having a cutting edge.

4. The hybrid probe/cutter instrument of claim 1, wherein the actuator mechanism is mounted to the handle.

5. The hybrid probe/cutter instrument of claim 4, wherein the actuator mechanism includes a slidable pad that is movable within a slot of the handle.

6. The hybrid probe/cutter instrument of claim 4, wherein the actuator mechanism includes a rotatable wheel.

7. The hybrid probe/cutter instrument of claim 1, wherein the actuator mechanism only translates the cutting device relative to the outer tube between the first position and the second position.

8. The hybrid probe/cutter instrument of claim 1, wherein the probe tip is not axially aligned with a body of the outer tube.

9. The hybrid probe/cutter instrument of claim 1, wherein the longitudinal portion includes a window, and the cutting device is configured to move within the window.

10. The hybrid probe/cutter instrument of claim 1, wherein a width of the longitudinal portion is substantially equal to a width of the curved portion.

11. The hybrid probe/cutter instrument of claim 1, wherein the cutting device is elongated.

12. The hybrid probe/cutter instrument of claim 1, wherein the cutting device is hook free.

13. The hybrid probe/cutter instrument of claim 1, wherein the cutting blade comprise a planar blade.

14. The hybrid probe/cutter instrument of claim 1, wherein the cutting blade slides between the first position and the second position within the longitudinal portion of the probe tip.

15. The hybrid probe/cutter instrument of claim 1, wherein the curved portion extends outside the diameter of the outer tube relative to the longitudinal axis.

16. A hybrid probe/cutter instrument for meniscal probing and cutting, comprising:
 a handle;
 an outer tube attached to the handle, the outer tube having a proximal end and a distal end;
 a probe tip comprising a hook at a most distal end of the outer tube and configured to hook tissue, wherein the hook comprises a longitudinal portion having an elongated slot and a curved portion extending from the longitudinal portion having another slot to receive a cutting device;
 the cutting device extending through the outer tube and housed within the outer tube, the cutting device configured to move within the elongated slot of the longitudinal portion from a first position proximal to the probe tip in which the cutting device is housed inside the outer tube to a second position in which the cutting device is received within the elongated slot formed in the probe tip, is nested within the another slot, and is exposed for cutting the tissue; and
 an actuator mechanism for actuating the cutting device from the first position to the second position.

17. The hybrid probe/cutter instrument of claim 16, wherein the cutting blade is interchangeable and disposable.

18. The hybrid probe/cutter instrument of claim 16, wherein the cutting blade is sterilizable.

19. A hybrid probe/cutter instrument, comprising:
 a handle;
 an outer tube attached to the handle at a first end portion, the outer tube is fully cannulated between the first end portion and a second end portion opposite from the first end portion, wherein the outer tube is stationary relative to the handle, the outer tube including a diameter and a longitudinal axis;
 a hooked probe tip comprising a hook disposed at the second end portion of the outer tube and configured to hook tissue, wherein the hook comprises a longitudinal portion having an elongated slot and a curved portion extending from the longitudinal portion having another slot to receive a cutting blade, a most distal surface of the hook of the outer tube is curved, and the longitudinal portion does not extend outside the diameter of the outer tube relative to the longitudinal axis;
 a cutting blade extending inside the outer tube and movable within the elongated slot of the longitudinal portion between a first position proximal to the probe tip in which the cutting blade is housed inside the outer tube and a second position in which the cutting blade is received within the elongated slot formed in the hooked probe tip, is nested within the another slot, and is exposed for cutting the tissue.

20. The hybrid probe/cutter instrument of claim 19, wherein the cutting blade has a diameter that decreases distally and terminates in a pointed tip.

21. The hybrid probe/cutter instrument of claim 19, comprising an actuator mechanism movably mounted to the handle and adapted to actuate the cutting blade between the first position and the second position.

22. The hybrid probe/cutter instrument of claim 21, wherein the actuator mechanism includes a slidable pad or a rotatable wheel that is movable relative to the handle.

23. The hybrid probe/cutter instrument of claim 19, wherein the actuator mechanism only translates the cutting device relative to the outer tube between the first position and the second position.

24. The hybrid probe/cutter instrument of claim 19, wherein the probe tip is not axially aligned with a body of the outer tube.

* * * * *